United States Patent [19]

Tirotta

[11] Patent Number: 5,431,158
[45] Date of Patent: Jul. 11, 1995

[54] ENDOSCOPY BREATHING MASK

[76] Inventor: Christopher F. Tirotta, 450 Grapetree Dr., No. 311, Key Biscayne, Fla. 33149

[21] Appl. No.: 268,723

[22] Filed: Jun. 30, 1994

Related U.S. Application Data

[63] Continuation of Ser. No. 49,417, Apr. 20, 1993, abandoned.

[51] Int. Cl.$^6$ .................. A61M 16/0; A62B 18/02
[52] U.S. Cl. .................. 128/206.21; 128/205.25; 128/200.26; 128/207.14
[58] Field of Search ............. 128/200.26, 203.29, 128/205.25, 206.21, 206.24, 206.26–207.12, 207.14, 207.17, 912, DIG. 26, 204.18

[56] References Cited

U.S. PATENT DOCUMENTS

| | | | |
|---|---|---|---|
| D.283,742 | 5/1986 | Hall | D29/7 |
| 1,000,706 | 8/1911 | Barnum | 128/206.12 |
| 1,139,850 | 5/1915 | Cunkle | 128/206.28 |
| 1,362,766 | 12/1920 | McGargill | 128/206.21 |
| 2,625,155 | 1/1953 | Engelder | 128/206.24 |
| 2,859,748 | 11/1958 | Hudson | D29/8 X |
| 2,860,632 | 11/1958 | Conti | 128/206.12 |
| 3,027,896 | 4/1962 | Newton | 128/380 X |
| 3,345,987 | 10/1967 | Ediin | D29/8 X |
| 3,620,214 | 11/1971 | Thacksten | D29/8 X |
| 3,905,361 | 9/1975 | Hewson et al. | 128/202.28 |
| 4,098,270 | 7/1978 | Dolby | 128/141 X |
| 4,256,099 | 3/1981 | Dryden | 128/200.26 |
| 4,328,797 | 5/1982 | Rollins et al. | 128/206.21 |
| 4,337,767 | 7/1982 | Yabata | 128/206.28 |
| 4,497,318 | 2/1985 | Michael | 128/202.28 |
| 4,580,556 | 4/1986 | Kondur | 128/206.28 |
| 4,719,911 | 1/1988 | Carrico | 128/206.29 |
| 4,848,331 | 7/1989 | Nothway-Meyer | 128/200.26 |
| 4,890,609 | 1/1990 | Wilson | 128/206.29 |
| 5,117,821 | 6/1992 | White | 128/206.12 |
| 5,197,463 | 3/1993 | Jeshuran | 128/207.14 |
| 5,199,424 | 4/1993 | Sullivan et al. | 128/204.18 |

*Primary Examiner*—Kimberly L. Asher
*Attorney, Agent, or Firm*—Richard C. Litman

[57] ABSTRACT

An endoscopic breathing mask configured to fit over the mouth and nose of a patient has an air tube positioned so that oxygen can be continuously and controllably introduced into the mask. A bite-block is provided for gripping by a patient's teeth. The bite-block is hollow to accommodate introduction of an endoscope thereinto. A Luer-lock port is provided for connection to a capnograph for monitoring respiration for apneic conditions that may lead to potentially fatal hypoxia. An adjustable strap is provided for securing the mask to the patient. A beaded edge surrounds the mask to provide rigidity as well as provide greater comfort to the patient. A plurality of openings is provided for the passive diffusion of a patients expiratory gases.

7 Claims, 1 Drawing Sheet

ENDOSCOPY BREATHING MASK

CROSS-REFERENCE TO RELATED APPLICATION

This application is a continuation of Application Ser. No. 08/049,417 filed on Apr. 20, 1993, now abandoned.

FIELD OF THE INVENTION

The present invention generally relates to respiratory devices capable of providing uninterrupted spontaneous respiratory assistance during concurrent endoscopic procedures.

BACKGROUND OF THE INVENTION

Endoscopic procedures involve the examination of the interior upper alimentary canal. Such procedures are often beset by the related problems of apnea (i.e. cessation of respiration) and hypoxia (i.e. reduced $O_2$ content in tissue and blood. Apnea if not detected and immediately redressed will produce the potentially fatal condition of hypoxia. In this light, the present invention generally provides an endoscopy-compatible respiratory face mask having means for the controllable delivery of oxygen throughout endoscopy as well as means to detect apneic conditions and thereby assist in the prevention of hypoxia.

Endoscopy is a medical procedure usually undertaken on an outpatient basis. The standard protocol generally requires intravenous (IV) sedation of the patient. A gastroenterologist usually administers the sedation for this procedure. Gastroenterologists, however, are not trained extensively in the specialized and esoteric field of anesthesiology. This deficiency, however, does not absolve them from employing the traditional standards of care normally attributed to trained anesthesiologists, vis-a-vis drug administration and patient monitoring. Part of the standard protocol involves the controlled and continuous administration of oxygen and the monitoring of respiration. Heretofore, no single endoscopy-compatible device has been developed that would effectively provide both oxygen administration and respiratory monitoring features without being cumbersome and/or interfering with an ongoing endoscopic procedure.

In the past, before acceptable anesthetic standards were applied to sites outside the operating room, administration of oxygen was occasionally achieved through insufflation, but in most cases omitted altogether. Monitoring of respiration was also commonly omitted. The results were numerous cases that ended in severe neurologic compromise, or death, as a result of the commencement and subsequent failure to redress an apneic condition leading to hypoxia.

Fortunately, the past trend has been reversed. Today, the basic underlying IV sedation protocol requires prevention of adverse respiratory events by administering oxygen to prevent hypoxia and early recognition of potentially critical incidence by the constant monitoring of patient respiration to detect foreboding indicia of an apneic condition. Regardless, the devices employed today to administer supplemental oxygen, i.e., nasal cannulas, simple face mask, etc., are nonetheless cumbersome and generally ineffective to maintain current standards during endoscopic procedures. While the problem has long existed, current respiratory devices either do not allow or interfere with access to the mouth, where the endoscope must be inserted. The present endoscopy mask has means for the controlled continuous administration of oxygen for spontaneous respiratory techniques combined with concomitant avenues for respiratory monitoring by capnographic methods. The configuration and design of these features on the mask facilitates endoscopic procedures as well as prevent the inconvenient interruption of the procedure once commenced.

More specifically, the mask provides a face mask with a bite block engageable by the teeth of a patient. The bite block has a hollow configuration to accommodate introduction of an endoscope. A Luer-lock port is provided for communicably accessible connection to a capnograph for respiratory monitoring. An air tube is positioned so that oxygen can be rapidly and controllably introduced into the mask. In view of these and other features, the invention may be effectively utilized to detect whether a patient is suffering from apnea so that a subsequent hypoxic condition can be immediately prevented. Since hypoxia may be redressed by manual procedures, such as repositioning a patient's head, it is unnecessary to remove the mask or otherwise interrupt an ongoing endoscopic procedure.

DESCRIPTION OF THE RELATED ART

A variety of masks for administering gases from a remote source were the subject of past patents. But despite the many variations, not one of these masks were able to surmount the problems relating to the onset of apneic or hypoxic conditions during endoscopic procedures.

Among the variety of masks are a number of early 20th century breathing devices developed for purposes other than that of rigidly controlled and monitored spontaneous respiratory administration during endoscopy.

U.S. Pat. No. 1,000,706, issued to Barnum on Aug. 15, 1911, focussed on the problems beset by coal miners, provides an unsophisticated and cumbersome respirator mask which was secured by several elastic straps and covered a large area of the bearer's lower face. Barnum's Coal Miner Mask employed a hose for supplying the miner with a constant supply of fresh air. Regardless, Barnum's mask was derived in a field totally unrelated to the field of sophisticated and rigidly controlled spontaneous respiratory administration and monitoring. Accordingly, Barnum's mask lacked several safeguards necessary for use in a clinical hospital setting.

U.S. Pat. No. 1,362,766, issued to McGargill on Dec. 21, 1920, provides a gas mask formed from a single piece of pliable transparent material shaped so as to cover the nose, mouth and eyes of a wearer. McGargill's Gas Mask was provided with an opening for insertion of a tube engageable by the teeth of a wearer. However, McGargill's Gas Mask, as with Barnum's Coal Mining Mask, was also derived in an unrelated field and would be unlikely to be considered for use as a clinical spontaneous respiratory device.

U.S. Pat. No. 1,139,850, issued to Conkle on May 18, 1915, shows a diver's face mask having an air inlet pipe and an air outlet pipe. Again, crafted in an unrelated field, Conkle never suggested addition of features that would make his diving mask suitable for modern day endoscopic procedures. Clearly, Conkle could not have converted his diving apparatus for endoscopic procedures or for spontaneous respiratory assistance without completely sacrificing the air-tight seal required for diving purposes.

Towards the mid 20th century and up to today, a flurry of masks were provided for use in various respiratory settings. While these masks provided several features, not one provided all features that would allow effective endoscopic procedures while providing both spontaneous respiratory assistance and means to monitor apnea, and thereby prevent the life threatening condition of hypoxia without interrupting ongoing procedures.

U.S. Pat. No. 2,859,748, issued to Hudson on Nov. 11, 1958, shows a breathing mask for administering oxygen to a patient. The mask covers only the patient's nose and has straps for securing the mask. A flexible tube was connected to the mask for introducing a regulated source of gas such as oxygen. Hudson did not disclose or suggest any means for detecting apnea so that subsequent hypoxic conditions may be averted.

U.S. Pat. No. 2,860,632, issued to Conti on Nov. 18, 1958, shows a bulky and uncomfortable hooded respirator mask having a configuration wherein air is supplied to the interior under pressure and is discharged through an opening in the front. Conti's hood lacked several features that would allow its use in endoscopic procedures that utilize spontaneous respiratory techniques.

U.S. Pat. No. 3,345,987, issued to Ediin on Apr. 13, 1964, provides a face mask that would cover only a patient mouth. Fluid under pressure is supplied to the lower portion by a tube. As with Hudson and Conti, Ediin did not disclose means for uninterruptedly detecting apnea for the purpose of preventing hypoxia. Ediin also does not disclose the use of a breathing tube orally engageable by the patient. The lack of such a feature is at cross purposes with endoscopic respiratory devices.

U.S. Pat. No 4,328,797, issued to Rollins on May 11, 1982, provides an oxygen mask having a naso-gastric tube aligned with the nostrils of a patient. U.S. Pat. No. 4,337,767, issued to Yahata on Jul. 6, 1982, shows an anesthesia mask having an opening for receiving anesthesia gas and an inflatable rib. U.S Pat. No. 4,580,556, issued to Konder on Apr. 8, 1980, shows a mask with scopes therein. U.S. Pat. No. 4,719,911, issued to Carrico on Jan. 11, 1988, shows an air filter mask having an orally engageable tube. Among other things, Rollins, Yahata, Konder and Carrico all fail to provide either a directly orally engageable bite-block or means for uninterruptedly detecting apnea for the purpose of preventing hypoxia.

In sum, not one of the above cited references, alone or in combination, disclose or suggest a device having all the features provided and claimed by the present invention.

SUMMARY OF THE INVENTION

Briefly, the present invention provides an improved face mask for assisting spontaneous patient respiration, where oxygen can be quickly and controllably administered to the patient in an easy and effective way, during a medical procedure involving intravenous sedation, such as endoscopy, without interfering with the procedure. A Luer-lock port is provided in the mask for communicably-accessible connection to a capnograph for monitoring the patient's respiration to detect the presence of apnea. An opening is provided in the mask to receive the oxygen or other respiratory gases. This opening is located near the nose of a patient and is integral with a flexible tube connected to a controllable supply of oxygen so that oxygen may be continuously supplied as needed to the patient in a controlled manner without removing the mask from the patient.

The mask has a bite-block orally engageable by the patient. If the patient is not conscious (which is likely) the bite-block serves to retain the mouth of the patient in an opened condition. The bite-block is hollow for reception of a fiberoptic endoscope. An external rib surrounds the mask to serve as a seal and to ensure patient comfort. Buckle slots are provided in the mask for adjustably attaching a flexible head encircling strap thereto. A malleable metal strip positioned so as to overlie the nose of a patient strengthens the mask. In accord with spontaneous respiratory techniques, a plurality of ring shaped openings are provided in the mask and positioned near the nose of a patient for egress of exhaust air.

Accordingly, one of the objects of the invention is to provide an improved face mask, including means for continuously and controllably administering oxygen to a patient during a medical procedure such as endoscopy without removal of the mask from the patient.

An additional object is to provide an improved face mask having an opening therein through which oxygen can be controllably introduced.

A further object is to provide a face mask having an opening connected to a tube which is connected to a controllable source of oxygen.

Another object is to provide a face mask having an opening located near the nose of a wearer and to one side thereof for receiving supplemental oxygen.

A further additional object is to provide a face mask having a bite block orally engageable by a patient to retain the mouth of the patient in an opened condition and to facilitate examination of the patient during a medical procedure such as endoscopy.

A still further object is to provide a face mask having a hollow bite-block adapted to receive suitable endoscopy apparatus such as an endoscope and means for assisting spontaneous patient respiration such that endoscopic examinations may be undertaken without interruptive and inconvenient removal of the mask during the examination.

An additional object is to provide a face mask having an external rib to serve as a seal and to facilitate patient comfort.

Another object is to provide a face mask having a Luer-lock port for connection to a capnograph for monitoring patient respiration whereby an apneic condition may be detected so that a subsequent hypoxic condition may be averted.

A further object is to facilitate spontaneous patient respiration by providing a face mask having openings therethrough for egress of exhaust air from the patient.

Another object is to provide a face mask having a malleable reinforcing metal strip positioned across a nose of a patient and an adjustable head encircling strap.

With these and other objects in view, which will more readily appear as the nature of the invention is better understood, the invention consists in the novel construction, combination and assembly of parts hereinafter more fully described, illustrated, and claimed with reference being made to the attached drawings.

BRIEF DESCRIPTION OF THE DRAWINGS

It is noted that similar reference characters designate corresponding parts throughout the several figures of the drawings.

DETAILED DESCRIPTION OF THE INVENTION

The present invention will now be further described in further detail with reference to the drawings.

Figure 1:
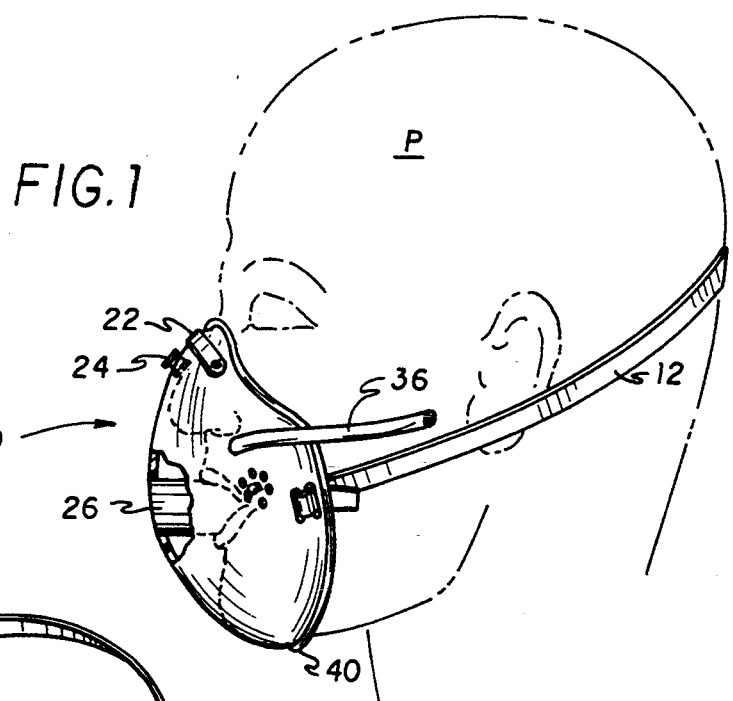
FIG. 1 is a left side perspective view of one embodiment of the inventive endoscopic breathing mask shown attached to the face of a patient.

FIG. 1 illustrates an improved face mask 10 in use attached to a patient P by a flexible strap 12. The mask 10 is formed from suitable plastic material which is non-permeable to both ambient air and typical respiratory gases and has sufficient flexibility so as to conform to the face of a patient. Aside from durability and resiliency, the plastic material selected should be non-reactive to any respiratory gases that would be used during endoscopic procedures. Also, while the invention does not require the use of clear plastic, a transparent material is preferred to the extent that such material allows visual observation of the patient's nasal and oral regions. Further, as shown in FIG. 1, the mask 10 is configured to fit comfortably and securely over both the patient's mouth and nose. It is believed that several configurations can be designed consistent with the purposes of the present invention. Accordingly, the figures are not intended to limit in anyway the invention to a specific shape.

Figure 2:
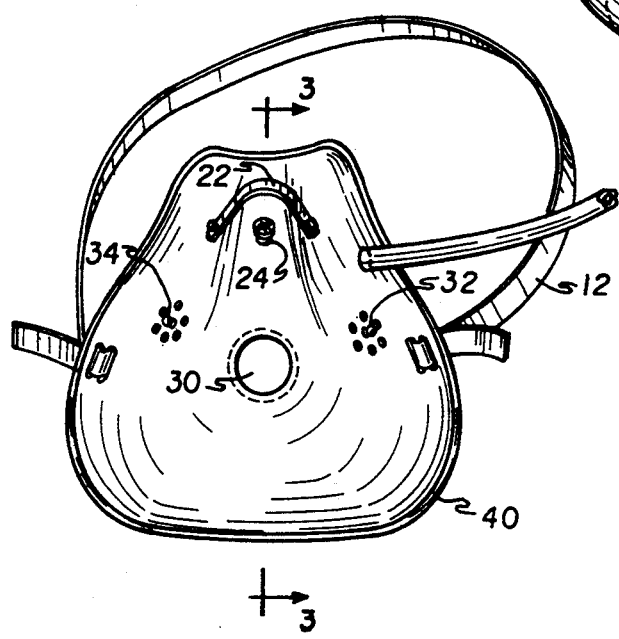
FIG. 2 is a front view of one embodiment of the inventive endoscopic breathing mask.

The mask may be secured to patient P in a number of ways. Of these ways, FIGS. 1 and 2 illustrate slots 14, 16 and 18, 20 provided in end portions of the mask 10 to threadably receive end portions of strap 12 for adjustably securing the mask to an associated face of a patient P. Such a securing means allows the mask to be self-secured to the patient and, thus, not encumbering any hospital staff personnel with this menial task.

As shown in FIGS. 1 and 2, an external rib 40 surrounds the entire peripheral edge of the mask 10 and serves to seal the mask 10 from entry of undesired outside air and facilitates patient comfort. In view of its function, the external rib 40 may be made of any material that would provide both a tight seal and sufficient elasticity and conformability to insure patient comfort. As with the material used for the mask 10, the material used for making external rib 40 should be non-reactive to any respiratory gases that would be used during endoscopic procedures.

Depending on the type of plastic material selected and the shape in which mask 10 is configured, no further reinforcement or supporting members would be necessary to utilize the mask 10. However, as depicted in FIGS. 1, 2, 3 and 4, a strip 22, preferably aluminum or other suitable material, is positioned so as to be adjacent the nose of a patient P and serves to reinforce the mask 10. The use of aluminum strip 22 also provides securing means additional to strap 12. Depending on the resiliency of the mask 10, the strip may be manually compressed or expanded based on the dimensions of the patient's nasal bridge. In other embodiments of the invention, it is envisioned that the position of the aluminum strip 22 would be adjustable.

As shown in FIGS. 1, 2, 3 and 4, Luer-Lock 24 is provided on the mask 10 for connection to a capnograph (not shown). Luer-Lock 24 provides a communicatively accessible link between the outside environment and the environment inside the mask 10. The link is "communicatively-accessible" because information concerning conditions on one side of the link (e.g., apnea) may be communicated to a point (e.g., capnographic monitor) on the other side by virtue of the interface provided by the link. The specific means and structural attributes providing this "communicative accessibility" will be chosen based on the specific capnographic monitors employed.

When a capnograph is attached to mask 10 via Luer-Lock 24, the mask can be used to monitor respiration of masked patient P without interruption of an ongoing endoscopic procedure. As shown in FIG. 1, the Luer-Lock 24 is positioned in close proximity to the bridge portion of mask 10. The gases in such an area are believed to be in less flux than in areas surrounding the mouth, openings 22, 24 and opening 38 of tube 36. The area is also closer to patient P's nostrils where expired gases are most likely to settle. In this location, more accurate and consistent capnographic monitoring is provided.

As shown in FIGS. 1, 2, 3 and 4, a flexible tube 36 has an end thereof attached to the mask 10 to cover an opening 38 therein. The tube 36 is connected to suitable means (not shown) for controllably and continuously introducing oxygen or other respiratory gases into the mask 10 in accord with spontaneous patient respiratory techniques.

Figure 3:
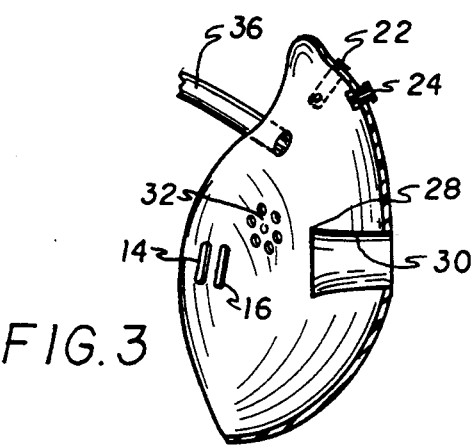
FIG. 3 is a lateral view of one embodiment of the inventive endoscopic breathing mask.
Figure 4:
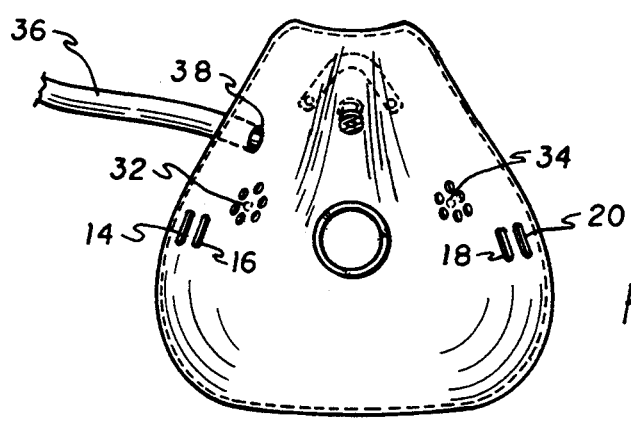
FIG. 4 is a back view of one embodiment of the inventive endoscopic breathing mask.

As shown on FIGS. 1 and 3, a bite-block 26 of hard plastic is permanently or temporarily attached to the mask 10 for engagement by the teeth of a patient P so as to retain the mouth of the patient P in an open condition. The bite-block 26 has a central opening 30 therein adapted to receive a scope therein (not shown) for use in endoscopy. An outwardly flared end 28 on the bite-block assists the retention of the bite-block in the mouth of a patient P. In other words, bite block 26 has a length extending into the patient's mouth only. FIGS. 1 and 3 taken together show a bit block having a flared outer end that terminates in the patient's mouth.

As shown in FIGS. 1, 2, 3 and 4, a grouping of openings 32, 34 are positioned near the nose of a patient P extend through mask 10 for egress of exhaust air from the mask 10. Since the mask 10 is to be used for spontaneous patient respiration, these opening 32, 34 allow expired $CO_2$-containing respiratory gas to passively diffuse out of the mask. In masks designed for controlled patient respiration, such expired gases are actively removed from the mask by external respiratory devices. Such active removal would not be possible if the known masks were fitted with passive respiratory gas outlet. Such masks usually require an air tight seal.

The number and the size of the openings will depend on the expected expiratory volume of the patient P. In other embodiments of the invention, it is envisioned that exhaust means can be provided that are adjustable. In such an embodiment the flow of oxygen into mask 10 would also be adjustable. In this manner, the respiration of the patient can be rigidly controlled and monitored.

In operation, prior to actually undertaking endoscopic procedures, the mask ports are all connected to their respective peripheral respiratory machinery: An oxygen source is connected to mask 10 via tube 36 at opening 38; endoscopy apparatus is prepared for insertion into mask 10 via bite-block 26; and a capnographic device is communicatively accessibly linked to the interior of mask 10 via Luer-Lock 24.

Once endoscopy is commenced, the masked patient P is constantly monitored for an apneic respiratory condition by the capnograph. Upon any indication that the patient P is suffering from an apneic condition, steps can be undertaken immediately to prevent the onset of any subsequent hypoxic condition without necessitating the untimely and inconvenient removal of the scope and consequently adversely affecting the ongoing procedure.

The inventive features of the above described mask can be incorporated into other mask systems such as Venturi mask, partial-rebreathing mask, or rebreathing masks.

It is to be understood that the present invention is not limited to the sole embodiment described above, but encompasses any and all embodiments within the scope of the following claims.

I claim:

1. A respiratory mask comprising:

a concave shaped body adapted to fit over the mouth and nose of a patient, said concave shaped body having at least a surrounding peripheral edge, an internal surface and an external surface, said concave shaped body being made of a substantially gas impermeable material and defining an inside area and an outside area when placed over the patient's mouth and nose, said inside area being in direct contact with said internal surface, said outside area being in direct contact with said external surface, said concave shaped body further having an above-nostril top bridge zone as defined when said mask is placed on the patient, and a below-nostril mouth zone as defined when said mask is placed on the patient;

a monitor port connected to said concave shaped body, said monitor port positioned in said above-nostril top bridge zone;

a respiratory gas inlet connected to said concave shaped body, said respiratory gas inlet positioned in said above nostril top bridge zone;

respiratory gas outlets formed in said concave shaped body and defining a plurality of openings on both sides of said concave shaped body communicating said inside area with said outside area;

and means for receiving an endoscope, said means comprising a bite block fixed to said concave shaped body, said bite block having a flared end which does not extend into a patient's throat when said mask is positioned on a patient.

2. The endoscopic respiratory mask of claim 1, wherein said respiratory gas outlet is adjustable such that said diffusion of said respiratory gases is controllable.

3. The endoscopic respiratory mask of claim 1, further comprising securing means for adjustably securing said concave shaped body to the patient.

4. The endoscopic respiratory mask of claim 3, wherein said securing means is at least one elastic strap attached to said concave shaped body.

5. The endoscopic respiratory mask of claim 1, wherein said substantially gas impermeable material is a transparent clear plastic.

6. The endoscopic respiratory mask of claim 1, further comprising a peripheral seal, said peripheral seal being attached to said peripheral edge of said concave shaped body.

7. The endoscopic respiratory mask of claim 1, further comprising a malleable metal strip, said metal strip located on said external surface of said concave body at said above-nostril bridge zone, said malleable metal strip adapted to be compressible onto and expandable out from the patient's nose when said mask is placed on the patient.

* * * * *